United States Patent
Bender et al.

(10) Patent No.: US 11,615,876 B2
(45) Date of Patent: Mar. 28, 2023

(54) PREDICTIVE MODEL FOR SUBSTANCE MONITORING AND IMPACT PREDICTION

(71) Applicant: International Business Machines Corporation, Armonk, NY (US)

(72) Inventors: Michael Bender, Rye Brook, NY (US); Rhonda L. Childress, Austin, TX (US); Edward Tyrone Childress, Austin, TX (US); Gregory J. Boss, Saginaw, MI (US)

(73) Assignee: INTERNATIONAL BUSINESS MACHINES CORPORATION, Armonk, NY (US)

( * ) Notice: Subject to any disclaimer, the term of this patent is extended or adjusted under 35 U.S.C. 154(b) by 538 days.

(21) Appl. No.: 16/161,659

(22) Filed: Oct. 16, 2018

(65) Prior Publication Data
US 2020/0118665 A1    Apr. 16, 2020

(51) Int. Cl.
*G16H 50/30*    (2018.01)
*G16H 50/70*    (2018.01)
*G16H 70/40*    (2018.01)
*G16H 20/30*    (2018.01)
*G06N 7/00*    (2006.01)

(52) U.S. Cl.
CPC ............ *G16H 20/30* (2018.01); *G06N 7/005* (2013.01); *G16H 50/30* (2018.01); *G16H 50/70* (2018.01); *G16H 70/40* (2018.01)

(58) Field of Classification Search
None
See application file for complete search history.

(56) References Cited

U.S. PATENT DOCUMENTS

| | | | |
|---|---|---|---|
| 8,725,311 | B1 | 5/2014 | Breed |
| 9,302,584 | B2 | 4/2016 | Walsh et al. |
| 10,825,567 | B1 * | 11/2020 | Wala ................. G16H 40/63 |
| 11,181,740 | B1 * | 11/2021 | Lewis ............... G02B 27/0172 |
| 2010/0131602 | A1 * | 5/2010 | Firminger ............. G06F 19/00 |
| | | | 709/206 |

(Continued)

OTHER PUBLICATIONS

Morisky et al, Predictive Validity of a Medication Adherence Measure in an Outpatient Setting, 2008, J. of Clinical Hypertension, V.10, pp. 348-354 (Year: 2008).*

(Continued)

*Primary Examiner* — Gregory Lultschik
*Assistant Examiner* — William G Lultschik
(74) *Attorney, Agent, or Firm* — Michael A. Petrocelli, Esq; Rachel L. Pearlman, Esq.; Heslin Rothenberg Farley Mesiti P.C.

(57) ABSTRACT

A method, computer program product, and a system where a processor(s) obtains data related to physical activities performed by an individual from a sensor(s) proximate to the individual. The processor(s) cognitively analyzes the data to identify baseline behavioral patterns of the individual, when the individual is engaged in each of the physical activities. The processor(s) obtains data indicating consumption of a substance by the individual at a first time. The processor(s) determines impacts of the consumption on the baseline behavioral patterns of the individual and generates a data structure (a predictive model) that includes expected deviations from the baseline behavioral patterns of the individual, when the individual has consumed the substance.

12 Claims, 7 Drawing Sheets

(56) References Cited

U.S. PATENT DOCUMENTS

| | | | | |
|---|---|---|---|---|
| 2012/0036103 A1* | 2/2012 | Stupp | ..................... | G16H 20/60 |
| | | | | 706/58 |
| 2012/0313785 A1* | 12/2012 | Hanson | .................. | G08B 23/00 |
| | | | | 340/573.1 |
| 2015/0199484 A1* | 7/2015 | Morris | ................... | G16H 50/20 |
| | | | | 705/2 |
| 2015/0257681 A1* | 9/2015 | Shuster | ................... | A61B 5/18 |
| | | | | 600/301 |
| 2016/0052391 A1* | 2/2016 | Walsh | ................. | B60K 28/066 |
| | | | | 340/575 |
| 2016/0188839 A1 | 6/2016 | Kaul et al. | | |
| 2017/0220772 A1* | 8/2017 | Vleugels | ............... | A61B 5/4875 |
| 2017/0293738 A1* | 10/2017 | Bender | .................. | G16H 70/40 |

OTHER PUBLICATIONS

Mell et al., "The NIST Definition of Cloud Computing", National Institute of Standards and Technology, U.S. Dept. of Commerce, NIST Special Publ. 800-145, Sep. 2011, 7 pages.

* cited by examiner

PREDICTIVE MODEL FOR SUBSTANCE MONITORING AND IMPACT PREDICTION

BACKGROUND

Various medications warn of side effects, but those side effects represent possibilities and are not personalized to a particular user of the medication. A user of a medication, when taking the medication, may also not be fully cognizant of the side effects that the medication is having on the cognitive abilities of the user. Understanding the side effects (or unintended effects) of the medication while under the influence of the medication can be extremely important to the user as a matter of safety. For example, while a cold remedy may warn of slight drowsiness, a user may experience more extreme side effects while would preclude certain activities (e.g., driving, otherwise operating heavy machinery) as safe undertakings. Individuals themselves may not be the best judges of the impacts of medications (or other substances that may cause impairment) on them, even if a warning appears on a package or in an insert. Many people ignore published warnings, because they can't identify or quantify the impacts a medication has on them. Thus, perhaps more important than knowing standard side effects, individuals would benefit from knowing the impacts of a medication on them, individually.

SUMMARY

Shortcomings of the prior art are overcome and additional advantages are provided through the provision of a method for predicting impacts of substances on an individual and the timing of those impacts. The method includes, for instance: continuously obtaining, by one or more processors, data related to physical activities performed by an individual from one or more sensors proximate to the individual; cognitively analyzing, by the one or more processors, the data to identify baseline behavioral patterns of the individual when the individual is engaged in each of the physical activities; obtaining, by the one or more processors, data indicating consumption of a substance by the individual at a first time; determining, by the one or more processors, based on comparing the continuously obtained data related to the physical activities performed by the individual prior to the first time to the continuously obtained data related to the physical activities performed by the individual subsequent to the first time, impacts of the consumption of the substance at the first time on the baseline behavioral patterns of the individual; and based on determining the impacts, generating, by the one or more processors, a data structure comprising expected deviations from the baseline behavioral patterns of the individual, when the individual has consumed the substance, wherein the data structure comprises a predictive model to utilize in determining one or more probabilities that the individual will exhibit one or more behaviors comprising the expected deviations, and determining an interval subsequent to consuming the substance in which the individual will exhibit the one or more behaviors.

Shortcomings of the prior art are overcome and additional advantages are provided through the provision of a computer program product for predicting impacts of substances on an individual and the timing of those impacts. The computer program product comprises a storage medium readable by a processing circuit and storing instructions for execution by the processing circuit for performing a method. The method includes, for instance: continuously obtaining, by the one or more processors, data related to physical activities performed by an individual from one or more sensors proximate to the individual; cognitively analyzing, by the one or more processors, the data to identify baseline behavioral patterns of the individual when the individual is engaged in each of the physical activities; obtaining, by the one or more processors, data indicating consumption of a substance by the individual at a first time; determining, by the one or more processors, based on comparing the continuously obtained data related to the physical activities performed by the individual prior to the first time to the continuously obtained data related to the physical activities performed by the individual subsequent to the first time, impacts of the consumption of the substance at the first time on the baseline behavioral patterns of the individual; and based on determining the impacts, generating, by the one or more processors, a data structure comprising expected deviations from the baseline behavioral patterns of the individual, when the individual has consumed the substance, wherein the data structure comprises a predictive model to utilize in determining one or more probabilities that the individual will exhibit one or more behaviors comprising the expected deviations, and determining an interval subsequent to consuming the substance in which the individual will exhibit the one or more behaviors.

Methods and systems relating to one or more aspects are also described and claimed herein. Further, services relating to one or more aspects are also described and may be claimed herein.

Additional features are realized through the techniques described herein. Other embodiments and aspects are described in detail herein and are considered a part of the claimed aspects.

BRIEF DESCRIPTION OF THE DRAWINGS

One or more aspects are particularly pointed out and distinctly claimed as examples in the claims at the conclusion of the specification. The foregoing and objects, features, and advantages of one or more aspects are apparent from the following detailed description taken in conjunction with the accompanying drawings in which:

DETAILED DESCRIPTION

Figure 1:
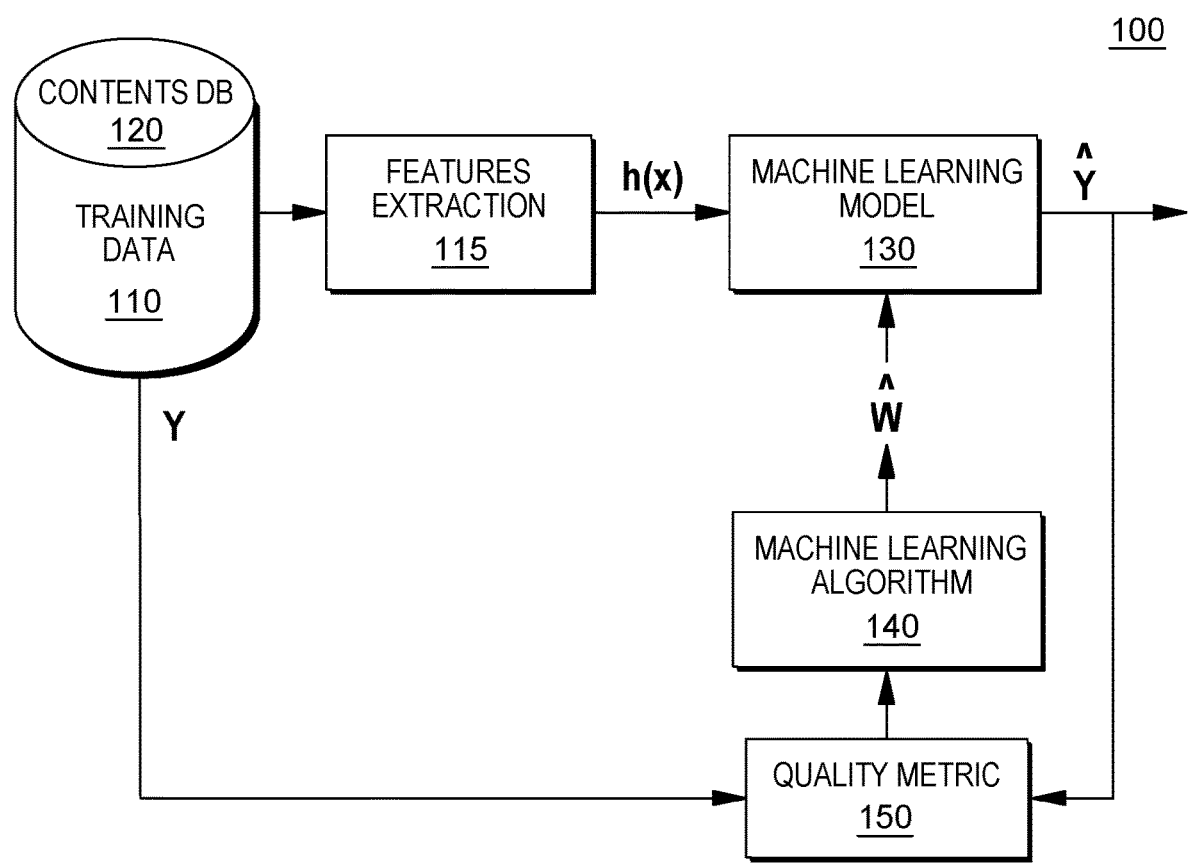
FIG. 1 is a workflow illustrating certain aspects of an embodiment of the present invention.

The accompanying figures, in which like reference numerals refer to identical or functionally similar elements throughout the separate views and which are incorporated in and form a part of the specification, further illustrate the present invention and, together with the detailed description of the invention, serve to explain the principles of the present invention. As understood by one of skill in the art, the accompanying figures are provided for ease of understanding and illustrate aspects of certain embodiments of the present invention. The invention is not limited to the embodiments depicted in the figures.

Figure 5:
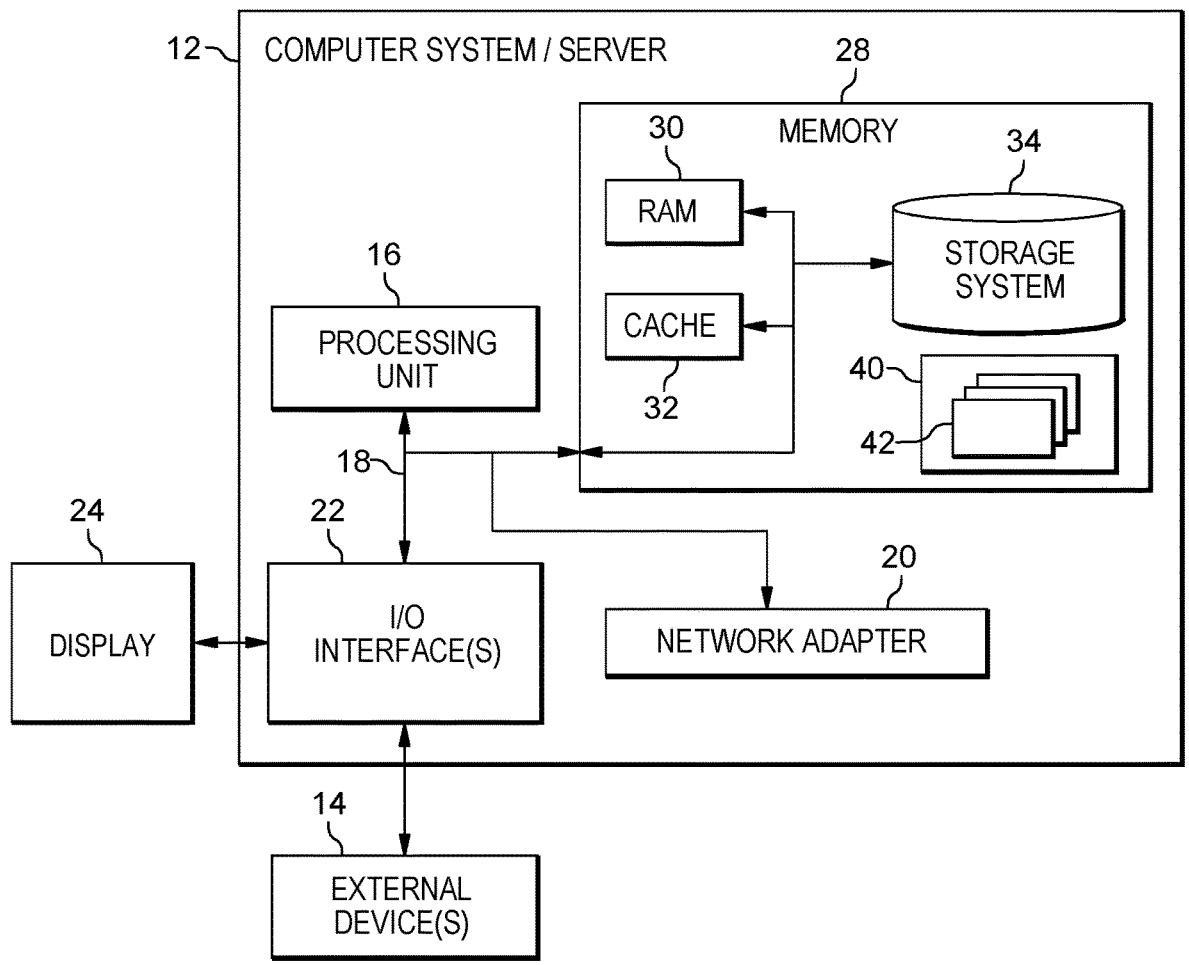
FIG. 5 depicts one embodiment of a computing node that can be utilized in a cloud computing environment.

As understood by one of skill in the art, program code, as referred to throughout this application, includes both software and hardware. For example, program code in certain embodiments of the present invention includes fixed function hardware, while other embodiments utilized a software-based implementation of the functionality described. Certain embodiments combine both types of program code. One example of program code, also referred to as one or more programs, is depicted in FIG. 5 as program/utility 40, having a set (at least one) of program modules 42, may be stored in memory 28.

Embodiments of the present invention include a computer-implemented method, a computer program product, and a computing system where program code executing on one or more processors identify effects (i.e., abnormalities in consumer/user behavior) of substances (e.g., medications, alcoholic beverages, etc.) consumed by an individual and generates alerts based on identified impacts of the substance on the individual, as well as the timing of those effects, relative to the consumption of the substance, by the individual. Thus, embodiments of the present invention include program code that provides data to an individual that enables the individual to learn, in a timely manner, that side effects of a substance consumed by this individual, are affecting the individual, and the timeframe in which these effects are anticipated to be in place, within a given level of confidence. In some embodiments of the present invention, the program code, within security constraints maintained by a user and/or administrator, transmits alerts and/or warnings to the individual, as well as to personnel providing assistance to the individual (e.g., medical staff, caregivers, emergency medical personnel, etc.). In some embodiments of the present invention, the program code utilizes various computing devices with which a user interacts, including but not limited to Internet of Things (IoT) devices, to establish a baseline of user behavior (e.g., patterns of movement, patterns of sleep, exercise, eye focus, balance, mood, gate, walking, driving, body reactions (e.g., yawning, eyes closing), etc.) in order to identify departures (abnormalities) from this baseline and determine if substances consumed by the user can be correlated to the changes, and what is the timing of the changes, relative to the consumption. In some embodiments of the present invention, program code identifies, via computing devices utilized by and proximate to the user (e.g., sensors, IoT devices, personal computing resources, image capture devices, biometric sensors, etc.) that a user has consumed (or otherwise self-administered) a given substance, thus providing the program code with a timeline to utilize when determining whether user behavior departs from the baseline established by the program code. Abnormal behaviors captured by the program code that can represent departures from the baseline can include, but are not limited to, departures from standard moods, interruptions in focus, deviations from established walking patterns, departures from expected driving habits, unexpected body reactions both in the presence and in the absence of stimulus, etc.

In embodiments of the present invention, the program code both establishes a baseline, and recognizes departures from that baseline, through machine learning. FIG. 1, which will be discussed herein, illustrates a machine learning process utilized by program code in embodiments of the present invention to formulate behavioral patterns (e.g., one or more baselines) for a given patient. Through machine learning, program code executing on one or more processors, in some embodiments of the present invention, learns when substances with potential side effects are consumed by an individual and contextual data surrounding the consumption, including but not limited to, if the substance was taken with other items, the volume consumed, and/or other dimensional information. The program code can then compare various aspects of the behavior of the individual during a specific activity being undertaken by the individual (e.g., walking, driving) to similar metrics related to the individual when performing the specific activity at other times. The program code, through machine learning, can identify a pattern which demonstrates the effect(s) with a certain level of confidence. Also based on this machine learning, the program code notifies the individual (and any other individual permitted by a security setting configured by the individual): 1) that the individual is affected by a known or unknown side effect of the consumed substance, and 2) a time window or expectation for when this effect will occur and/or dissipate. Thus, in embodiments of the present invention, program code provides predictions, within various confidence levels, related to side effects, and the duration of the side effects that can be experienced by a given individual, after the individual consumes a given substance.

Embodiments of the present invention are inextricably tied to computing and provide significantly more than existing technological approaches to monitoring the effects of substance consumption on the behavior of the consumers. First, embodiments of the present invention enable program code executing on one or more processors to exploit the interconnectivity of various systems, as well as utilize various computing-centric data analysis and handling techniques, in order to generate a continuously-updated predictive model. The program code applies the predictive model in order to provide customized temporal alerts to users identified by the program code. Both the interconnectivity of the computing systems utilized and the computer-exclusive data processing techniques utilized by the program code enable various aspects of the present invention. Second, embodiments of the present invention provide significantly more functionality than existing approaches to ascertaining the effects of substances on consumers of the substances because, in embodiments of present invention, the program code provides predictive data related to the consumption, including but not limited to, predicting the duration of a given (identified, including expected and unexpected) side effect on an individual, within an established degree of confidence. Some existing approaches track, generally, the health of a given individual, by utilizing biometric sensors, including monitoring whether an individual is adhering to a defined medical regimen and/or monitoring the blood/alcohol level of an individual. Other approaches track fatigue level of an individual after consuming a substance. However, in embodiments of the present invention, the program code provides significantly more functionality, including but not limited to: 1) the program code determines when a substance was consumed by an individual; 2) the program code monitors activities of the individual to determine when and how behaviors of the individual deviate from expected (machine learned) program code-generated patterns, thus identifying a previously known or unknown side effect experienced by the individual; 3) the program code determines the context in which the individual is experiencing the identified side effect (e.g., what medications, supplements, food and/or combination contributed to the side effect); and 4) the program code predicts the timeline of the impact of the identified side effect on the individual, based on the behavioral patterns and the context.

Figure 2:
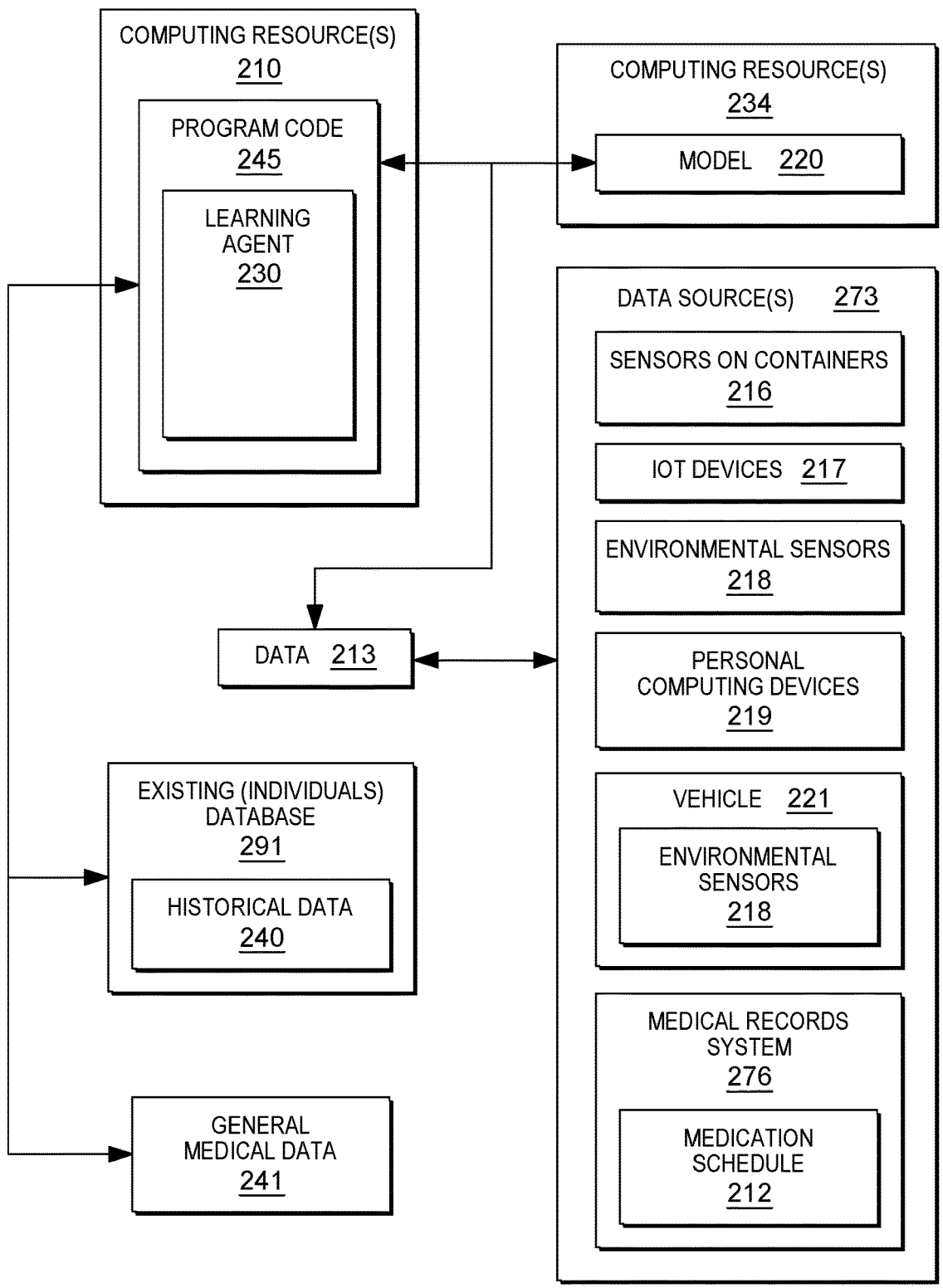
FIG. 2 is an illustration of a technical environment into which various aspects of an embodiment of the present invention can be implemented.

FIG. 2 is an environment 200 into which various aspects of some embodiments of the present invention can be implemented. The environment includes 200 various computing devices, including one or more computing resources 210 that execute program code 245 that generates or updates a model 220, based on machine learning (e.g., via a cognitive and/or learning agent 230), and utilizes the model 200 to identify a previously known or unknown side effect of a substance (e.g., food, medication, beverage, etc.), experienced by an individual who consumed the substance at a given time, and determines the context in which the individual is experiencing the identified side effect (e.g., what medications, supplements, food and/or combination contributed to the side effect) and predicts the timeline of the impact of the identified side effect on the individual, based on the behavioral patterns and the context. For illustrative purposes only, the model 220 is depicted in FIG. 2 as being housed on a separate computing resource 234 from the one or more computing resources 210 that execute the program code 245. This is a non-limiting example of an implementation, as the program code 245 and the model 220 can also share a computing resource. Likewise, in the illustrated implementation, the program code 245 is illustrated as comprising the learning agent 230. However, various modules of the program code 245 can be executed on varied resources in various embodiments of the present invention, thus, the learning agent 230 and the program code 245 can be separate modules.

In embodiments of the present invention, program code 245 utilizes various data 213 from various sensors, cameras (or other image capture devices), biometric feedback, manual inputs, and/or a medication schedule 212, to identify a substance consumed by an individual, and the timing of the consumption of that substance. Data 213 can be provided from various data sources 273, including but not limited to, sensors on containers 216 (e.g., smart containers) utilized to dispense the substance, personal computing devices 219, utilized by an individual and proximate to an individual, continuous monitoring systems, such as Internet of Things (IoT) devices 217, and environmental sensors 218 in various environments, including sensors inside a vehicle 221 being operated by the individual.

As stated above, the data 213 can include data collected from one or more continuous monitoring systems and also sensors that provide data at specific points in time to the program code 245 (e.g., sensors on containers 216), can include Internet of Things (IoT) devices 217 and other environmental (e.g., environmental sensors 218), and/or personal computing devices (e.g., personal computing devices 219) with sensors. As understood by one of skill in the art, the Internet of Things (IoT) is a system of interrelated computing devices, mechanical and digital machines, objects, animals and/or people that are provided with unique identifiers and the ability to transfer data over a network, without requiring human-to-human or human-to-computer interaction. These communications are enabled by smart sensors, which include, but are not limited to, both active and passive radio-frequency identification (RFID) tags, which utilize electromagnetic fields to identify automatically and to track tags attached to objects and/or associated with objects and people. Smart sensors, such as RFID tags, can track environmental factors related to an object, including but not limited to, temperature and humidity. The smart sensors can be utilized to measure temperature, humidity, vibrations, motion, light, pressure and/or altitude. IoT devices 217 also include individual activity and fitness trackers, which include (wearable) devices or applications that include smart sensors for monitoring and tracking fitness-related metrics such as distance walked or run, calorie consumption, and in some cases heartbeat and quality of sleep and include smartwatches that are synced to a computer or smartphone for long-term data tracking. In some embodiments of the present invention, the program code 245 executed by the one or more computing resources 210 utilizes IoT devices 217, such as personal fitness trackers and other types of motion trackers, both to establish a baseline (e.g., generate and update a model 220 through machine learning optionally via a learning agent 230) for a user when engaged in a specific activity (e.g., walking, driving) and to determine whether the user, who is engaged in the specific activity, is deviating from that activity, based on experiencing a side effect of a substance that the user consumed in advance of or during the activity. IoT devices also include Smart home devices, digital assistants, and home entertainment devices, which comprise examples of environmental sensors 218. Because the smart sensors in IoT devices 217 carry unique identifiers, a computing system that communicates with a given sensor can identify the source of the information. Within the IoT, various devices can communicate with each other and can access data from sources available over various communication networks, including the Internet. Thus, the program code 245 in some embodiments of the present invention utilizes data obtained from various IoT devices 217 to generate or update the model 220 utilized by the program code 245 to predict side effects experienced by individuals within a given timeframe of consumption, within a certain degree of confidence.

In some embodiments of the present invention, the data 213 includes biometric and/or physiological data from continuous monitoring and includes, but is not limited to, cardiovascular measures (e.g., heart rate, blood pressure, blood oxygen saturation, and respiration), body positioning and movement data (e.g., rest versus activity data), body temperature, and environmental conditions of the environment of the patient (e.g., ambient light and/or noise).

The program code 245 updates the model 220 in real-time, upon receipt of the data 213, including sensor data that deviates from the model 220. Program code 245 of the learning agent 230 utilizes this data 213 to continually learn and updates the patterns that form the model 220. An event that would trigger the program code 245 to update the model 220 in real-time would be the data 213 indicating that an individual is not experiencing expected side effects while participating in an activity for which side effects are predicted, by the program code 245, to occur, within the timeframe in which the program code 245 predicted that the side effects would occur.

As aforementioned, in embodiments of the present invention, the program code 245 executing on the one or more computing resources 210 determines that a given individual has consumed a given substance, at a given time. The program code 245 can make this determination based on receiving data 213 from a number of sources, including but not limited to, sensors on containers 216 utilized to dispense the substance, personal computing devices 219, utilized by an individual and proximate to an individual, continuous monitoring systems, such as Internet of Things (IoT) devices 217, and/or environmental sensors 218 in various environments, including sensors inside a vehicle 221 being operated by the individual. The program code 245 can also receive this data from other types of computing devices, including image capture devices proximate to the user, including (with proper security permissions) embedded in the personal computing devices 219. In some embodiments of the present invention, the program code 245 predicts that a user will take a substance, based on obtaining medication scheduling information 212 from outside sources including, but not limited to, electronic medical records, and/or a treatment scheduling system 276. In order to obtain medical information, embodiments of the present invention include security preferences, such that a user and/or an administrator can approve permission (and limit permission) to and electronic medical records, and/or a treatment scheduling system. The program code 245 can utilize this medication scheduling information 212 to predict when, at a future time proximate to receiving specified medication, the patient can anticipate experiencing a side effect. In some embodiments of the present invention, when the program code 245 initializes the model 220, the program code 245 obtains historical data 240 that the program code 245 can utilize to improve pattern detection and prediction (generating and updating the model 220) for the given individual. For example, the program code 245 of the learning agent 230 can incorporate data from an existing database 291 for similar use case history to determine the likely effects of the various substances (e.g., medications) on individuals in the existing database 291 and the possible side effects experienced by the individual within a given time window of consuming the substance. The program code 245 can adjust the model 220 in accordance with these learned patterns.

In some embodiments of the present invention, the program code 245 accesses general medical data 241 in order to correlate a behavior of an individual with a side effect of a substance consumed by the individual. For example, in some embodiments of the present invention, the program code 245 tracks consumption of the individual (e.g., food, drink, medication, etc.). The program code 245 continuously monitors behaviors of the individual and determines, based on baseline behavior patterns of the individual, established by the program code 245 and based on receiving data 213 from sensors inside a vehicle 221, the individual is driving in a manner inconsistent with the individual's (safe) driving patterns. For example, in some embodiments of the present invention, the program code 245 determines that an individual has deviated from safe driving patterns by utilizing a cognitive analysis agent (e.g., Watson) to analyze data received as speech via a vocal input on a personal computing device 219 utilized by the individual while in the vehicle. For example, the program code 245 supplements its analytics with speech analytics from a cognitive agent to determine that the individual's speech is slurred. Given that the program code 245 has previously learned, via the learning agent 230, patterns and/or known behaviors of the individual, including speech patterns of the individual, the program code 245 utilizes data analytics to identify an abnormality in the learned patterns. The program code 245 accesses the general medical data 241 (which can be a specialized database requiring permissions and/or a resource that is publicly available via an Internet connection) and determines, based on the consumption of the individual in advance of the driving, which substance consumed by the individual carries a side effect that would impact driving ability. The program code 245 updates the model 220 to indicate the findings and also can alert the individual of the issue.

The program code 245 executing on one or more computing resources 210 applies machine learning algorithms to generate and train algorithms to generate a model 220 the program code 245 utilizes to predict side effects experienced by a given individual within a given time of consuming a given substance, within an established degree of confidence (and/or as a binary value). In the aforementioned initialization stage, the program code 245 trains these algorithms, based on patterns for a given individual (and/or across all individuals with certain shared attributes).

FIG. 1 is an example of a machine learning training system 100 that can be utilized to perform cognitive analyses of various inputs, including the general initialization data, the data 213, and optionally, the historical data 240. Training data utilized to train the model in embodiments of the present invention can also include historical data that is personalized to the individual, including but not limited to: 1) data 213 (e.g., physiological data from patient monitoring including cardiovascular measures such as heart rate, blood pressure, blood oxygen saturation, respiration, rest versus activity data from body movement and body position, temperature, ambient light, noise readings, and data gathered from monitoring activities and motion of the individual); 2) medication scheduling information 212 and/or data indicators (e.g., from sensors) that an individual has definitely consumed a substance.

Returning to FIG. 1, the program code in embodiments of the present invention performs a cognitive analysis to generate data structures, including algorithms utilized by the program code to identify side effects experienced by various individuals and to predict the likelihood and durations of those side effects. Machine learning (ML) solves problems that cannot be solved with numerical means alone. In this ML-based example, program code extracts various features/attributes from training data 140 (e.g., historical data collected from various data sources relevant to the individual and general data), which may be resident in one or more databases 120 comprising individual-related data and general data. The features are utilized to develop a predictor function, h(x), also referred to as a hypothesis, which the program code utilizes as a machine learning model 130. In identifying side effects experienced by individuals within various time windows of consuming a substance in the training data 110, the program code can utilize various techniques including, but not limited to, mutual information, which is an example of a method that can be utilized to identify features in an embodiment of the present invention. Further embodiments of the present invention utilize varying techniques to select features (elements, patterns, attributes, etc.), including but not limited to, diffusion mapping, principal component analysis, recursive feature elimination (a brute force approach to selecting features), and/or a Random Forest, to select the attributes related to various side effects of substances experienced by individuals and the duration of those side effects relative to the individuals consuming the substances. The program code may utilize a machine learning algorithm 140 to train the machine learning model 130 (e.g., the algorithms utilized by the program code), including providing weights for the conclusions, so that the program code can train the predictor functions that comprise the machine learning model 130. The conclusions may be evaluated by a quality metric 150. By selecting a diverse set of training data 110, the program code trains the machine learning model 130 to identify and weight various attributes (e.g., features, patterns) that correlate to various side effects experienced by an individual, the timeline of when the side effects will commence, relative to consuming a substance, and the predicted duration of those side effects.

Returning to FIG. 2, the model 220 generated by the program code 245 can be self-learning, as the program code 245 updates the model 220 based on passive feedback received from the data 213, related to monitoring the individual. For example, when the program code 245 determines that an individual is driving erratically at a given time that was not previously predicted by the model 220 (e.g., within a window of time after consuming a substance at which the program code 245 predicted that this side effect would have subsided), the program code 245 utilizes a learning agent 230 to update the model 220 to reflect this unpredicted side effect, in order to improve predictions in the future. Program code 245 comprising a learning agent 230 cognitively analyzes the data deviating from the modeled expectations and adjusts the model 220 in order to increase the accuracy of the model, moving forward.

In some embodiments of the present invention, program code 245 executing on one or more computing resources 210, utilizes existing cognitive analysis tools or agents to tune the model 220, based on data obtained from the various data sources, including the data 213. Some embodiments of the present invention utilize IBM Watson® as the learning agent 230 (i.e., cognitive agent). IBM Watson® is a product of International Business Machines Corporation. IBM Watson® is a registered trademark of International Business Machines Corporation, Armonk, N.Y., US. In embodiments of the present invention, the program code 245 interfaces with IBM Watson® APIs to perform a cognitive analysis of obtained data, in some embodiments of the present invention, the program code 245 interfaces with the application programming interfaces (APIs) that are part of a known cognitive agent, such as the IBM Watson® Application Program Interface (API), a product of International Business Machines Corporation, to determine impacts of data 213 and other data on behavioral patterns (of individuals upon consumption of various substances) and to update the model 220, accordingly.

In some embodiments of the present invention, the program code 245 trains aspects of the IBM Watson® Application Program Interface (API) to learn the relationships between physiological elements from the sensors 213 and the behavioral patterns of the patient. For example, in some embodiments of the present invention, the program code 245 can determine that a given individual experiences slurred speech (based on attempted vocal inputs of the individual to a personal computing devices 219).

Utilizing an existing cognitive agent, such as IBM Watson® expands the type of patient data that the program code 245 can integrate into the model 220. For example, sensors data 213 can include documentary, visual, and audio data, which the program code 245 can process, based on its utilization of IBM Watson®. Specifically, in some embodiments of the present invention, certain of the APIs of the IBM Watson® API comprise a cognitive agent (e.g., learning agent 230) that includes one or more programs, including, but are not limited to, natural language classifiers, Retrieve and Rank (i.e., a service available through the IBM Watson® Developer Cloud that can surface the most relevant information from a collection of documents), concepts/visual insights, trade off analytics, document conversion, and/or relationship extraction. In an embodiment of the present invention, one or more programs analyze the data obtained by the program code 245 across various sources utilizing one or more of a natural language classifier, retrieve and rank APIs, and trade off analytics APIs. The IBM Watson® Application Program Interface (API) can also provide audio related API services, in the event that the collected data includes audio, which can be utilized by the program code 245, including but not limited to speech recognition, natural language processing, text to speech capabilities, and/or translation.

The program code 245 can provide predictions for a given individual as varying values. In some embodiments of the present invention, the program code 245 calculates a binary value for the individual, which represents whether a given substance is predicted to effect a given individual during a given time period. In other embodiments of the present invention, the program code 245 provides the user with an indicator of one or more of: 1) a probability that given substance will effect a given individual during a given current and/or future period of time; and/or 2) a confidence level related to the prediction. As discussed above, in embodiments of the present invention, should the individual's behavior and/or other monitored values deviate from the model 220 predictions, based on continuously monitoring the individual (e.g., utilizing IoT devices 217 and other computing devices including environmental and/or personal sensors), the program code 245 can immediately update the model 220 and/or, in some embodiments of the present invention, alert the individual and/or other users designated by the individual to be alerted. For example, in some embodiments of the present invention, alerts can be sent to medical personnel treating the individual.

In some embodiments of the present invention, the program code 245 utilizes a neural network to analyze collected data relevant to an individual to generate the model 220 utilized to predict the effects of consuming a given substance within a given time period, on the individual, and the anticipated length of time the effect will be experienced by the individual. Neural networks are a biologically-inspired programming paradigm which enable a computer to learn from observational data, in this case, sensor data, and/or medication scheduling information. This learning is referred to as deep learning, which is a set of techniques for learning in neural networks. Neural networks, including modular neural networks, are capable of pattern (e.g., state) recognition with speed, accuracy, and efficiency, in situations where data sets are multiple and expansive, including across a distributed network, including but not limited to, cloud computing systems. Modern neural networks are non-linear statistical data modeling tools. They are usually used to model complex relationships between inputs and outputs or to identify patterns (e.g., states) in data (i.e., neural networks are non-linear statistical data modeling or decision making tools). In general, program code 245 utilizing neural networks can model complex relationships between inputs and outputs and identify patterns in data. Because of the speed and efficiency of neural networks, especially when parsing multiple complex data sets, neural networks and deep learning provide solutions to many problems in multiple source processing, which the program code 245 in embodiments of the present invention accomplishes when obtaining data and generating a model for predicting effects of a variety of substances on a variety of individuals, during designated time windows, within a given level of confidence.

Some embodiments of the present invention may utilize a neural network (NN) to predict future states of a given patient. Utilizing the neural network, the program code 245 can predict the likelihood an individual experiences a given side effect from consuming a given substance at a first time, at a subsequent time. The program code 245 obtains (or derives) data related to the individual from various sources to generate an array of values (possible behaviors/side effects) to input into input neurons of the NN. Responsive to these inputs, the output neurons of the NN produce an array that includes the predicted side effects during predicted time periods. The program code 245 can automatically transmit notifications related to the predicted side effects based on the perceived validity.

In some embodiments of the present invention, a neuromorphic processor or trained neuromorphic chip can be incorporated into the computing resources executing the program code 245. One example of a trained neuromorphic chip that is utilized in an embodiment of the present invention is the IBM® TrueNorth chip, produced by International Business Machines Corporation. IBM® is a registered trademark of International Business Machines Corporation, Armonk, N.Y., U.S.A. Other names used herein may be registered trademarks, trademarks or product names of International Business Machines Corporation or other companies.

The IBM® TrueNorth chip, also referred to as TrueNorth, is a neuromorphic complementary metal-oxide-semiconductor (CMOS) chip. TrueNorth includes a manycore network on a chip design (e.g., 4096 cores), each one simulating programmable silicon "neurons" (e.g., 256 programs) for a total of just over a million neurons. In turn, each neuron has 256 programmable synapses that convey the signals between them. Hence, the total number of programmable synapses is just over 268 million (2^28). Memory, computation, and communication are handled in each of the 4096 neurosynaptic cores, so TrueNorth circumvents the von-Neumann-architecture bottlenecks and is very energy-efficient.

Below are some non-limiting examples of the functionality of various aspects of some embodiments of the present invention can be utilized in various situations. To illustrate these examples, reference is made to the environment 200 of FIG. 2. The use of the environment 200 of FIG. 2 is not meant to impose any limitations, but merely to provide an illustration for various aspects.

In an environment 200 into which aspects of the present invention are implemented, an individual takes an antihistamine. The program code 245 executing on one or more computing resource 210 determines that the individual has taken the antihistamine based on obtaining data reflecting this activity from sensors on the container 216 in which the antihistamine is stored. The program code 245 obtains data from the sensors on the container 216 identifying the individual, the antihistamine dosage consumed (or removed from the container 216), and the timing of this consumption. After taking the antihistamine, behaviors of the individual are monitored by various sensors in the environment, including IoT devices 217, environmental sensors 218, and/or personal computing devices 219. In this example, a personal laptop with an image capture device is among the personal computing devices 219 continuously monitoring the individual. (In some embodiments of the present invention, rather than continuously monitoring, the program code 245 initiates the monitoring based on obtaining data indicating that the individual has consumed a substance.) Based on obtaining data transmitted from the image capture device of the individual's laptop, the program code 245 determines that after three hours have elapsed, the individual can no longer focus the individual's eyes on the screen. Although general medical data available to the program code 245 indicates that that this effect of the antihistamine only lasts for six hours, the program code 245 determines, via monitoring the individual, that the individual is experiencing this visual impairment for nine hours. The program code 245 utilizes this information to train the model 220. Thus, at a future time, when the individual consumes the antihistamine, the program code 245 generates a warning to the individual, optionally populated in a graphical user interface (GUI) of a personal computing device 219 of the individual, or through another electronic notification means, recommending to the user that the user refrain from driving for nine hours.

In an environment 200 into which aspects of the present invention are implemented, an individual takes a medication with side effects warnings that indicate a possibility that the individual may not be able to operate a motor vehicle effectively while under the influence of the medication. The program code 245 determines that the individual has ingested the medication (e.g., based on the program code 245 communicating with sensors on the container 216 and/or obtaining medication scheduling information 212). After taking the medication, program code 245 obtains information from sensors on personal computing devices 219 of the individual, carried by the individual, while the individual is walking (e.g., a mobile phone, a personal fitness tracker, or other device with motion sensing capabilities, including a gyroscope). Data 213 from the personal computing devices 219, indicates, to the program code 245, that the movement of the individual while walking deviates from expected motion patterns (e.g., as indicated in the model 220). For example, the program code 245 can determine, based on data 213 from the sensors and a comparison with the model 220, that the gate of the individual is outside an expected range of motion (e.g., machine learned baseline activity patterns). Additionally, data obtained by the program code 245 from sensors inside a vehicle 221 being operated by the individual indicate that the individual is not checking the vehicle's mirror at an expected frequency, while operating the vehicle. In some embodiments of the present invention, the program code 245, through a computing device proximate to the individual, alerts the individual that the individual is driving unsafely and should not drive after taking the medication. In some embodiments of the present invention, the program code 245 updates the model 220 to indicate the side effects experienced by the individual, such that the program code 245 can alert the individual going forward, should the individual consume the medication at a later date. In some embodiments of the present invention, the program code 245 sends alerts that highlight the risks to driving for the individual after consumption of the substance. In some embodiments of the present invention, the program code 245 updates medication scheduling information 212 to recommend (or implement) changes to dosage of the medication, based on the analysis of the side effects experienced by the individual.

In some embodiments of the present invention, the program code 245 provides warnings to individuals contemporaneous with the individuals experiencing unanticipated side effects and recommends behaviors to mitigate negative impacts of continuing various activities. For example, an individual may consume herbs that the individual has presumed to produce no side effects. The program code 245 identifies the timing of this consumption and the consumption of the herbs based on monitoring the individual (with the individual's acquiescence), based on the individual manually entering that the individual is consuming a particular type of tea (that includes the herbs) in a nutritional tracker executing on a personal computing device 219 of the individual. A period of time (e.g., four hours), after consumption of the tea, the program code 245, executing on the one or more computing resources 210 determines, based on data 213 received from various sensors, including data from sensors inside a vehicle 221, that the individual is not operating the vehicle 221 in a manner consistent with established patterns (e.g., the individual is unable to keep the vehicle moving in a straight line). The program code 245 determines, based on accessing general medical data 241 from one or more computing resources, an herb, in the tea, carries a warning related to driving after consumption. The program code 245 transmits a warning to the individual, via a personal computing device 219 of the user, to get off the road immediately and not to continue driving after consuming this herb—the program code 245 can also identify the herb to the individual.

In some embodiments of the present invention, the program code 245 can determine that behaviors of an individual deviate from expected behavioral patterns or baselines, but there is no substance that is responsible for this issue. Based on continuous monitoring of an individual through various sensors in an environment 200, program code 245 learns the behaviors of an individual, but can also contextualize this behavior. Sensors in an environment 200 can monitor factors such as rest versus activity data from body movement and body position, temperature, ambient light, and noise readings. Thus, when in some embodiments of the present invention, the program code 245 determines that an individual is walking in a manner inconsistent with established patterns, but the individual has consumed no substance that would produce these effects, the program code 245 can determine that exhaustion is the reason for the changes in movement, rather than consumption of a substance. In some embodiments of the present invention, the program code 245 can send an alert to the individual and advise the individual to rest.

Figure 3:
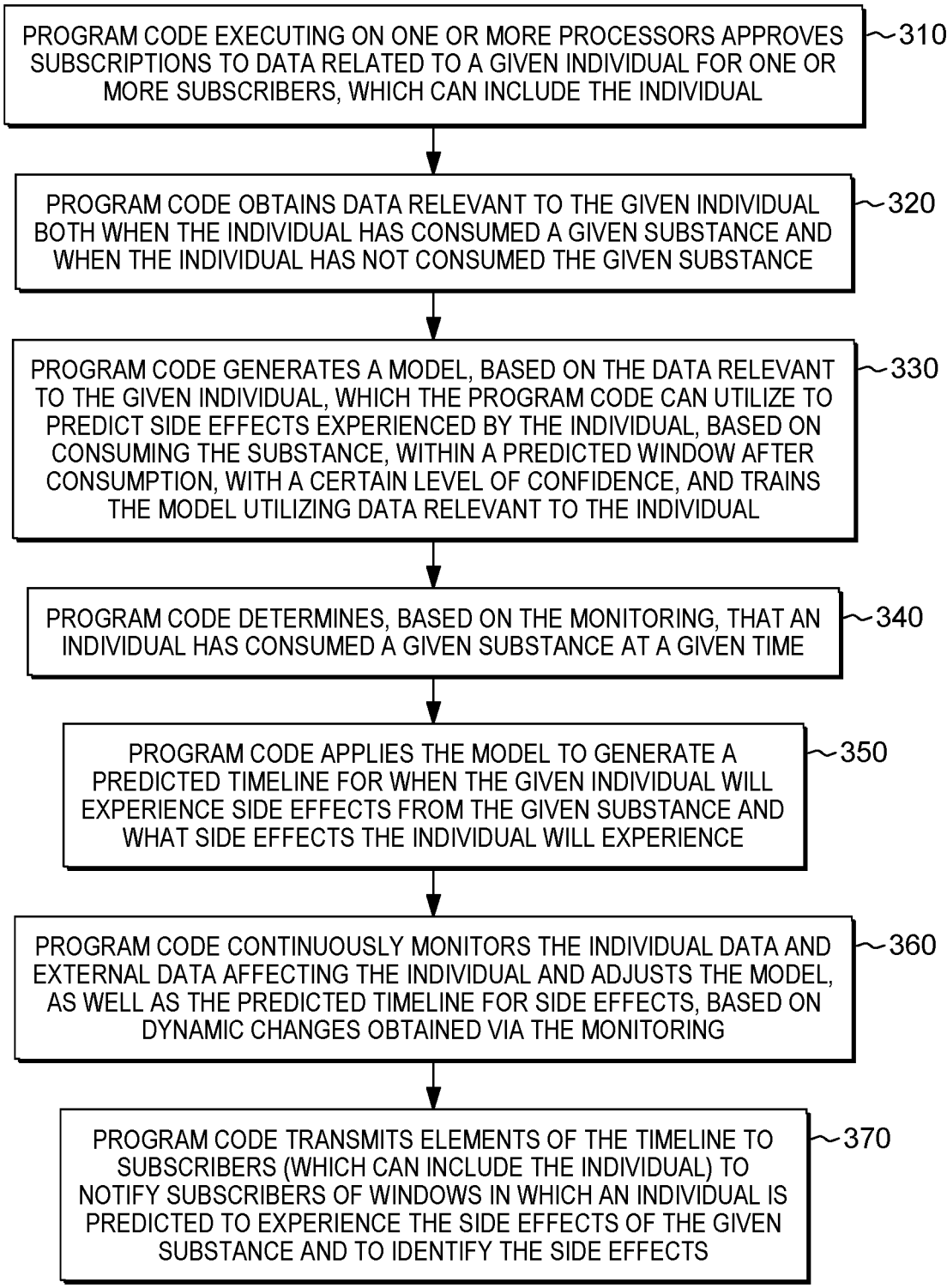
FIG. 3 is a workflow illustrating certain aspects of an embodiment of the present invention.

FIG. 3 is a workflow 300 that illustrates certain aspects of some embodiments of the present invention. In some embodiments of the present invention, program code executing on one or more processors approves subscriptions to data related to a given individual for one or more subscribers, which can include the individual (310). The subscriber authorization process can include submissions being individually approved by an administrator and/or automatic approval of subscribers based on the subscribers providing relevant credentials through an interface to a computing node accessible to the one or more processors executing the program code. Both subscription procedures and alerts provided by the program code conform to best privacy and security practices. For example, alerts provided by the program code, to which a user subscribes, in some embodiments of the present invention, do not include any personally identifiable information, but, rather, indicate probabilities that an individual will experience certain side effects during set periods of time. This indication can be provided by the program code in a user-friendly manner, through a graphical user interface on a client computing device, such as utilizing colors to indicate confidence levels associated with the prediction (e.g., red/yellow/green).

The program code obtains data relevant to the given individual both when the individual has consumed a given substance and when the individual has not consumed the given substance (320). Data relevant to an individual includes data that the program code obtains from a variety of sources, including but not limited to physical sensor data relevant to activity of the individual (e.g., heart rate, muscle tension, oxygen levels, breathing, and/or motion detection). The program code obtains this data both before, during, and after consumption of the substance by the individual, such that the program code can generate a baseline for values of the individual while engaging in various activities and contrast this baseline with values obtained by the sensors for the individual, when engaging in various activities, obtained after the individual has consumed the given substance.

As understood by one of skill in the art, the program code, through training and iterative processing, can establish baseline values that represent behavioral patterns for a given individual. The program code can cognitively analyze the data to identify these patterns and integrate the patterns into the predictive model. Certain values obtained by the program code can deviate without expected ranges from the baseline, but as the overall activity or health of the individual changes, the baseline value can also change. In embodiments of the present invention, the program code can obtain updated data describing the movement or habits of the individual when the individual is engaged in a given activity (e.g., walking, swimming, running, etc.) and update various baselines that comprise the model based on the changes. The program code modifies the generated predictive windows for side effects based on continuously obtaining data, including but not limited to, sensor data and/or scheduled events. The program code updates baselines based on threshold changes (changes of a certain degree and/or of a certain quantity). In embodiments of the present invention, based on receiving an outlier event (e.g., via sensor data), the program code can override an existing prediction and change the prediction without changing the model. Based on receiving a threshold number of outliers, the program code can update the model itself.

The program code generates a model, based on the data relevant to the given individual, which the program code can utilize to predict side effects experienced by the individual, based on consuming the substance, within a predicted window after consumption, with a certain level of confidence, and trains the model utilizing data relevant to the individual (330). As part of generating the model, the program code trains or initializes the model, as discussed in FIGS. 1-2. The program code can initialize the model based on data related to the overall health and activity of the individual, including but not limited to, medication information, as related to individuals that the program code determines are similar to the individual, as well as, in some embodiments of the present invention, historical data related to the individual. As depicted in FIG. 2, the program code can utilize general medical data 241 as a source of training data to utilize in training the model. By utilizing this general medical data 241, the program code can improve the pattern detection and learning utilized by the program code to generate the prediction model. General medical data 241, including data relevant to certain medications that the individual can be scheduled to receive or ingests (on-the-fly), as indicated by data 213, would assist in prediction of side effect timing because the general medical data 241 would indicate, for example, the windows in which individuals are expected to experience side effects, the medication doses that are predicted to generate the side effects, and identifications of possible side effects, which the program code could utilize in an initial model and refine based on monitoring responses from the specific individual.

The program code determines, based on the monitoring, that an individual has consumed a given substance at a given time (340). As explained in FIG. 2, the program code can make this determination from receiving data 213 from various sources and/or based on obtaining medication scheduling information 212 from a medical records system 276. In some embodiments of the present invention, the individual may input (e.g., through a nutritional or other application executing on a personal computing device 219), that the individual has consumed a substance and the program code can obtain this information from the nutritional or other application.

The program code applies the model to generate a predicted timeline for when the given individual will experience side effects from the given substance and what side effects the individual will experience (350). Upon generating the timeline, the program code continues to monitor the data sources relevant to the patient and adjust the model and the timeline, based on the changes to the model, to reflect a most current understanding of intervals in the timeline where there exists a threshold probability that the patient will experience the identified side effects, from a given substance. The timeline reflects windows in which various activities that the individual may participate in would be impacted by the individual having consumed the substance. For example, during the timeline, the abilities of an individual to drive can be predicted to be impaired. In some embodiments of the present invention, if sensors the individual and environmental factors within a vicinity of the individual indicate that an individual is either experiencing or not experiencing a given side effect within at a time where the opposite is predicted by the program code, the program code updates the model such that the model reflects this deviation, with decay rates of prediction accuracy.

The program code continuously monitors the individual data and external data affecting the individual and adjusts the model, as well as the predicted timeline for side effects, based on dynamic changes obtained via the monitoring (360). In embodiments of the present invention, when the program code obtains data from sensors, in real-time, which conflicts with modeled patterns, the program code can either override the predictions of the model and/or update the model to comport with the anomalies. Based on the one-off change or the model revision, the program code updates the timeline.

The program code transmits elements of the timeline to subscribers (which can include the individual) to notify subscribers of windows in which an individual is predicted to experience the side effects of the given substance and to identify the side effects (370). In some embodiments of the present invention, the program code may send alerts to an individual when the program code determines that the individual is about to engage in an activity that is predicted to be affected by the individual having consumed a substance within a given timeframe relative to the activity. In some embodiments of the present invention, the program code transmits a warning to a physician and/or emergency medical personnel in relation to the taken medication, in response to identifying that the individual is experiencing side effects of a medication (e.g., in response to the program code identifying an abnormality in an established pattern of the individual, subsequent to the individual taking the medication).

Figure 4:
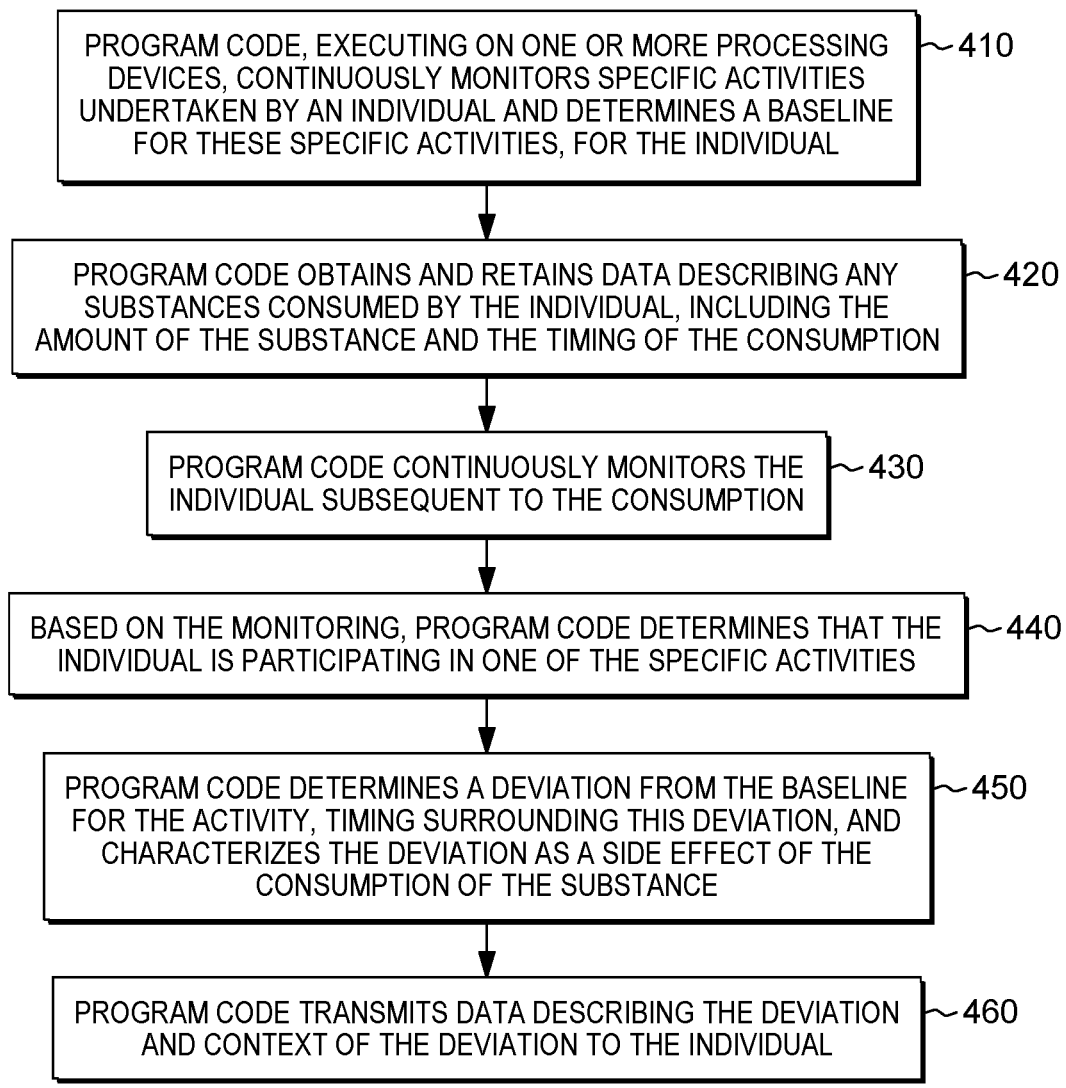
FIG. 4 is a workflow illustrating certain aspects of an embodiment of the present invention.

FIG. 4 is a workflow 400 that illustrates various aspects of some embodiments of the present invention. This workflow 400 illustrates an application of certain aspects of the present invention such that the determinations by the program code involve analyzing specific activities undertaken by an individual. As such, in some embodiments of the present invention, program code, executing on one or more processing devices, continuously monitors specific activities undertaken by an individual (e.g., walking, driving) and determines a baseline for these specific activities, for the individual (410). In the illustrated embodiment, the program code obtains and retains data describing any substances consumed by the individual, including the amount of the substance and the timing of the consumption (420). In some embodiments of the present invention, the program code obtains this data via manual entry into a computing device communicatively couples to the processor(s) executing the program code. In some embodiments of the present invention, the program code obtains this data utilizing a smart container (bottle, plate, cup, etc.). In some embodiments of the present invention, the program code obtains this data from environmental and/or personal sensors. The program code continuously monitors the individual subsequent to the consumption (430). Based on the monitoring, the program code determines that the individual is participating in one of the specific activities (440). The program code determines a deviation from the baseline for the activity, timing surrounding this deviation, and characterizes the deviation as a side effect of the consumption of the substance (450). The program code can perform an analysis that compares readings of sensors monitoring the individual with readings taken at difference times, to identify differences based on time ingested, dosage and amount of impact of the substance on the person. The program code transmits data describing the deviation and context of the deviation to the individual (and/or prescribing doctor, and/or pharmaceutical manufacturer of the substance) (460).

Embodiments of the present invention include a computer-implemented method, a computer program product, and a computer system where program code executing on one or more processors continuously obtains data related to physical activities performed by an individual from one or more sensors proximate to the individual. The program code cognitively analyzes the data to identify baseline behavioral patterns of the individual when the individual is engaged in each of the physical activities. The program code obtains data indicating consumption of a substance by the individual at a first time. The program code determines, based on comparing the continuously obtained data related to the physical activities performed by the individual prior to the first time to the continuously obtained data related to the physical activities performed by the individual subsequent to the first time, impacts of the consumption of the substance at the first time on the baseline behavioral patterns of the individual, Based on determining the impacts, the program code generates a data structure comprising expected deviations from the baseline behavioral patterns of the individual, when the individual has consumed the substance, where the data structure comprises a predictive model to utilize in determining one or more probabilities that the individual will exhibit one or more behaviors comprising the expected deviations, and determines an interval subsequent to consuming the substance in which the individual will exhibit the one or more behaviors.

In some embodiments of the present invention, the program code obtains data indicating consumption of the substance by the individual at a second time. The program code determines, based on applying the data structure, a probability that the individual will exhibit one or more behaviors comprising the expected deviations, and an interval subsequent to the second time in which the individual will exhibit the one or more behaviors. The program code can also transmit the probability and the interval subsequent to the second time, to the individual, via a computing device comprising a portion of the one or more sensors.

In some embodiments of the present invention, the one or more sensors monitor biometrics, behaviors, and motion of the individual when the individual is engaged in the physical activities.

In some embodiments of the present invention, the program code obtains data indicating consumption of the substance by the individual at a second time. The program code determines, based on applying the data structure, a probability that the individual will exhibit one or more behaviors comprising the expected deviations, and an interval subsequent to the second time in which the individual will exhibit the one or more behaviors. Based on the probability exceeding a pre-defined threshold, the program code transmits the probability and the interval subsequent to the second time, to the individual, via a computing device comprising a portion of the one or more sensors. The computing device that includes the portion of the one or more sensors can be an Internet of Things device.

In some embodiments of the present invention, the data indicating consumption of the substance by the individual at the first time comprises contextual data describing the consumption.

In some embodiments of the present invention, the contextual data comprises a quantity of the substance consumed by the individual at the first time.

In some embodiments of the present invention, the data related to physical activities performed by an individual is selected from the group consisting of: physiological data, heart rate, blood pressure, blood oxygen saturation, respiration, movement data indicating a restful state, movement data indicating an active state, temperature, ambient light readings, eye focus, and noise readings.

In some embodiments of the present invention, the program code obtaining the data indicating consumption of the substance by the individual at the first time comprises obtaining a schedule of planned consumption times for the substance, where the first time comprises a planned consumption time, where the schedule is accessible via a communication connection to at least one computing resource, and where the at least one computing resource is communicatively coupled to the one or more processors.

In some embodiments of the present invention, the program code obtaining the data indicating consumption of the substance by the individual at the first time comprises obtaining the data from a device selected from the group consisting of: at least one sensor of the one or more sensors and an image capture device proximate to the individual.

In some embodiments of the present invention, the program code obtaining the data indicating consumption of the substance by the individual at the first time comprises capturing the data from a personal computing device utilized by the individual, where the one or more processors are communicatively coupled to the personal computing device.

In some embodiments of the present invention, the program code obtains additional data related to one or more additional behaviors experienced by other individuals after consuming the substance. The program code cognitively analyzes the additional data, by applying the predictive model to determine if the additional data is consistent with the baseline behavioral patterns. Based on determining that the additional data is inconsistent with the baseline behavioral patterns, the program code updates the one or more behaviors to include a portion of the one or more additional behaviors. The program code can also update the model, based on the additional data.

Referring now to FIG. 5, a schematic of an example of a computing node, which can be a cloud computing node 10. Cloud computing node 10 is only one example of a suitable cloud computing node and is not intended to suggest any limitation as to the scope of use or functionality of embodiments of the invention described herein. Regardless, cloud computing node 10 is capable of being implemented and/or performing any of the functionality set forth hereinabove. In an embodiment of the present invention the one or more computing resources 210 (FIG. 2) that execute program code, the personal computing devices 219 (FIG. 2), the IoT devices 217 (FIG. 2), the resource(s) executing the learning agent 230 (FIG. 2), the electronic medical records, and/or a treatment scheduling system 276 (FIG. 2), and/or the resource(s) housing the general medical data 24 (FIG. 2) can each be understood as a cloud computing node 10 (FIG. 5) and if not a cloud computing node 10, then one or more general computing nodes that include aspects of the cloud computing node 10. Various examples of these resources may, together, comprise a hybrid cloud.

In cloud computing node 10 there is a computer system/server 12, which is operational with numerous other general purpose or special purpose computing system environments or configurations. Examples of well-known computing systems, environments, and/or configurations that may be suitable for use with computer system/server 12 include, but are not limited to, personal computer systems, server computer systems, thin clients, thick clients, handheld or laptop devices, multiprocessor systems, microprocessor-based systems, set top boxes, programmable consumer electronics, network PCs, minicomputer systems, mainframe computer systems, and distributed cloud computing environments that include any of the above systems or devices, and the like.

Computer system/server 12 may be described in the general context of computer system-executable instructions, such as program modules, being executed by a computer system. Generally, program modules may include routines, programs, objects, components, logic, data structures, and so on that perform particular tasks or implement particular abstract data types. Computer system/server 12 may be practiced in distributed cloud computing environments where tasks are performed by remote processing devices that are linked through a communications network. In a distributed cloud computing environment, program modules may be located in both local and remote computer system storage media including memory storage devices.

As shown in FIG. 5, computer system/server 12 that can be utilized as cloud computing node 10 is shown in the form of a general-purpose computing device. The components of computer system/server 12 may include, but are not limited to, one or more processors or processing units 16, a system memory 28, and a bus 18 that couples various system components including system memory 28 to processor 16.

Bus 18 represents one or more of any of several types of bus structures, including a memory bus or memory controller, a peripheral bus, an accelerated graphics port, and a processor or local bus using any of a variety of bus architectures. By way of example, and not limitation, such architectures include Industry Standard Architecture (ISA) bus, Micro Channel Architecture (MCA) bus, Enhanced ISA (EISA) bus, Video Electronics Standards Association (VESA) local bus, and Peripheral Component Interconnect (PCI) bus.

Computer system/server 12 typically includes a variety of computer system readable media. Such media may be any available media that is accessible by computer system/server 12, and it includes both volatile and non-volatile media, removable and non-removable media.

System memory 28 can include computer system readable media in the form of volatile memory, such as random access memory (RAM) 30 and/or cache memory 32. Computer system/server 12 may further include other removable/non-removable, volatile/non-volatile computer system storage media. By way of example only, storage system 34 can be provided for reading from and writing to a non-removable, non-volatile magnetic media (not shown and typically called a "hard drive"). Although not shown, a magnetic disk drive for reading from and writing to a removable, non-volatile magnetic disk (e.g., a "floppy disk"), and an optical disk drive for reading from or writing to a removable, non-volatile optical disk such as a CD-ROM, DVD-ROM or other optical media can be provided. In such instances, each can be connected to bus 18 by one or more data media interfaces. As will be further depicted and described below, memory 28 may include at least one program product having a set (e.g., at least one) of program modules that are configured to carry out the functions of embodiments of the invention.

Program/utility 40, having a set (at least one) of program modules 42, may be stored in memory 28 by way of example, and not limitation, as well as an operating system, one or more application programs, other program modules, and program data. Each of the operating system, one or more application programs, other program modules, and program data or some combination thereof, may include an implementation of a networking environment. Program modules 42 generally carry out the functions and/or methodologies of embodiments of the invention as described herein.

Computer system/server 12 may also communicate with one or more external devices 14 such as a keyboard, a pointing device, a display 24, etc.; one or more devices that enable a user to interact with computer system/server 12; and/or any devices (e.g., network card, modem, etc.) that enable computer system/server 12 to communicate with one or more other computing devices. Such communication can occur via Input/Output (I/O) interfaces 22. Still yet, computer system/server 12 can communicate with one or more networks such as a local area network (LAN), a general wide area network (WAN), and/or a public network (e.g., the Internet) via network adapter 20. As depicted, network adapter 20 communicates with the other components of computer system/server 12 via bus 18. It should be understood that although not shown, other hardware and/or software components could be used in conjunction with computer system/server 12. Examples include, but are not limited to: microcode, device drivers, redundant processing units, external disk drive arrays, RAID systems, tape drives, and data archival storage systems, etc.

It is to be understood that although this disclosure includes a detailed description on cloud computing, implementation of the teachings recited herein are not limited to a cloud computing environment. Rather, embodiments of the present invention are capable of being implemented in conjunction with any other type of computing environment now known or later developed.

Cloud computing is a model of service delivery for enabling convenient, on-demand network access to a shared pool of configurable computing resources (e.g., networks, network bandwidth, servers, processing, memory, storage, applications, virtual machines, and services) that can be rapidly provisioned and released with minimal management effort or interaction with a provider of the service. This cloud model may include at least five characteristics, at least three service models, and at least four deployment models.

Characteristics are as follows:

On-demand self-service: a cloud consumer can unilaterally provision computing capabilities, such as server time and network storage, as needed automatically without requiring human interaction with the service's provider.

Broad network access: capabilities are available over a network and accessed through standard mechanisms that promote use by heterogeneous thin or thick client platforms (e.g., mobile phones, laptops, and PDAs). Resource pooling: the provider's computing resources are pooled to serve multiple consumers using a multi-tenant model, with different physical and virtual resources dynamically assigned and reassigned according to demand. There is a sense of location independence in that the consumer generally has no control or knowledge over the exact location of the provided resources but may be able to specify location at a higher level of abstraction (e.g., country, state, or datacenter). Rapid elasticity: capabilities can be rapidly and elastically provisioned, in some cases automatically, to quickly scale out and rapidly released to quickly scale in. To the consumer, the capabilities available for provisioning often appear to be unlimited and can be purchased in any quantity at any time.

Measured service: cloud systems automatically control and optimize resource use by leveraging a metering capability at some level of abstraction appropriate to the type of service (e.g., storage, processing, bandwidth, and active user accounts). Resource usage can be monitored, controlled, and reported, providing transparency for both the provider and consumer of the utilized service.

Service Models are as follows:

Software as a Service (SaaS): the capability provided to the consumer is to use the provider's applications running on a cloud infrastructure. The applications are accessible from various client devices through a thin client interface such as a web browser (e.g., web-based e-mail). The consumer does not manage or control the underlying cloud infrastructure including network, servers, operating systems, storage, or even individual application capabilities, with the possible exception of limited user specific application configuration settings.

Platform as a Service (PaaS): the capability provided to the consumer is to deploy onto the cloud infrastructure consumer-created or acquired applications created using programming languages and tools supported by the provider. The consumer does not manage or control the underlying cloud infrastructure including networks, servers, operating systems, or storage, but has control over the deployed applications and possibly application hosting environment configurations.

Infrastructure as a Service (IaaS): the capability provided to the consumer is to provision processing, storage, networks, and other fundamental computing resources where the consumer is able to deploy and run arbitrary software, which can include operating systems and applications. The consumer does not manage or control the underlying cloud infrastructure but has control over operating systems, storage, deployed applications, and possibly limited control of select networking components (e.g., host firewalls).

Deployment Models are as follows:

Private cloud: the cloud infrastructure is operated solely for an organization. It may be managed by the organization or a third party and may exist on-premises or off premises.

Community cloud: the cloud infrastructure is shared by several organizations and supports a specific community that has shared concerns (e.g., mission, security requirements, policy, and compliance considerations). It may be managed by the organizations or a third party and may exist on-premises or off-premises.

Public cloud: the cloud infrastructure is made available to the general public or a large industry group and is owned by an organization selling cloud services.

Hybrid cloud: the cloud infrastructure is a composition of two or more clouds (private, community, or public) that remain unique entities but are bound together by standardized or proprietary technology that enables data and application portability (e.g., cloud bursting for load-balancing between clouds).

A cloud computing environment is service oriented with a focus on statelessness, low coupling, modularity, and semantic interoperability. At the heart of cloud computing is an infrastructure that includes a network of interconnected nodes.

Figure 6:
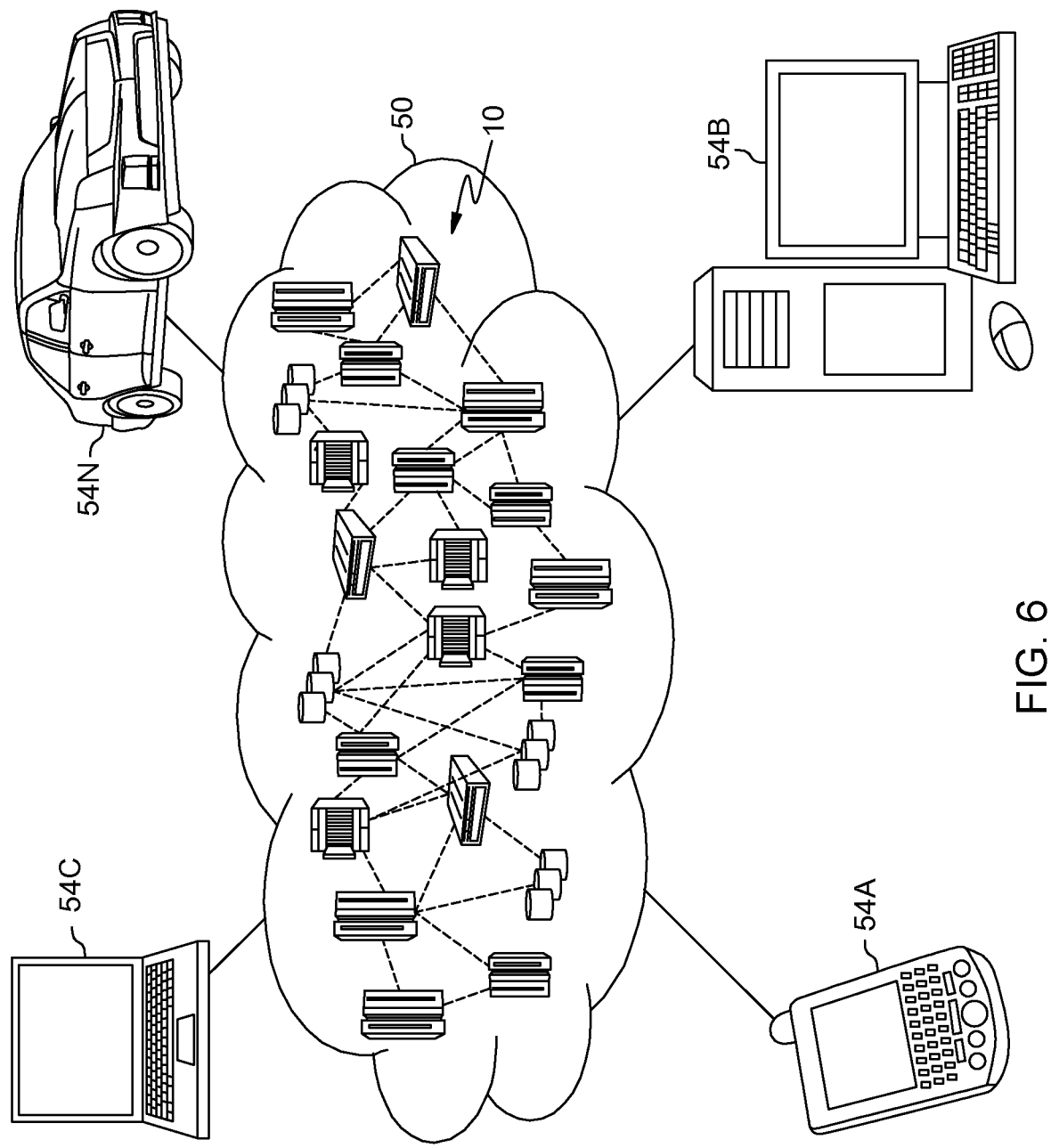
FIG. 6 depicts a cloud computing environment according to an embodiment of the present invention.

Referring now to FIG. 6, illustrative cloud computing environment 50 is depicted. As shown, cloud computing environment 50 includes one or more cloud computing nodes 10 with which local computing devices used by cloud consumers, such as, for example, personal digital assistant (PDA) or cellular telephone 54A, desktop computer 54B, laptop computer 54C, and/or automobile computer system 54N may communicate. Nodes 10 may communicate with one another. They may be grouped (not shown) physically or virtually, in one or more networks, such as Private, Community, Public, or Hybrid clouds as described hereinabove, or a combination thereof. This allows cloud computing environment 50 to offer infrastructure, platforms and/or software as services for which a cloud consumer does not need to maintain resources on a local computing device. It is understood that the types of computing devices 54A-N shown in FIG. 6 are intended to be illustrative only and that computing nodes 10 and cloud computing environment 50 can communicate with any type of computerized device over any type of network and/or network addressable connection (e.g., using a web browser).

Figure 7:
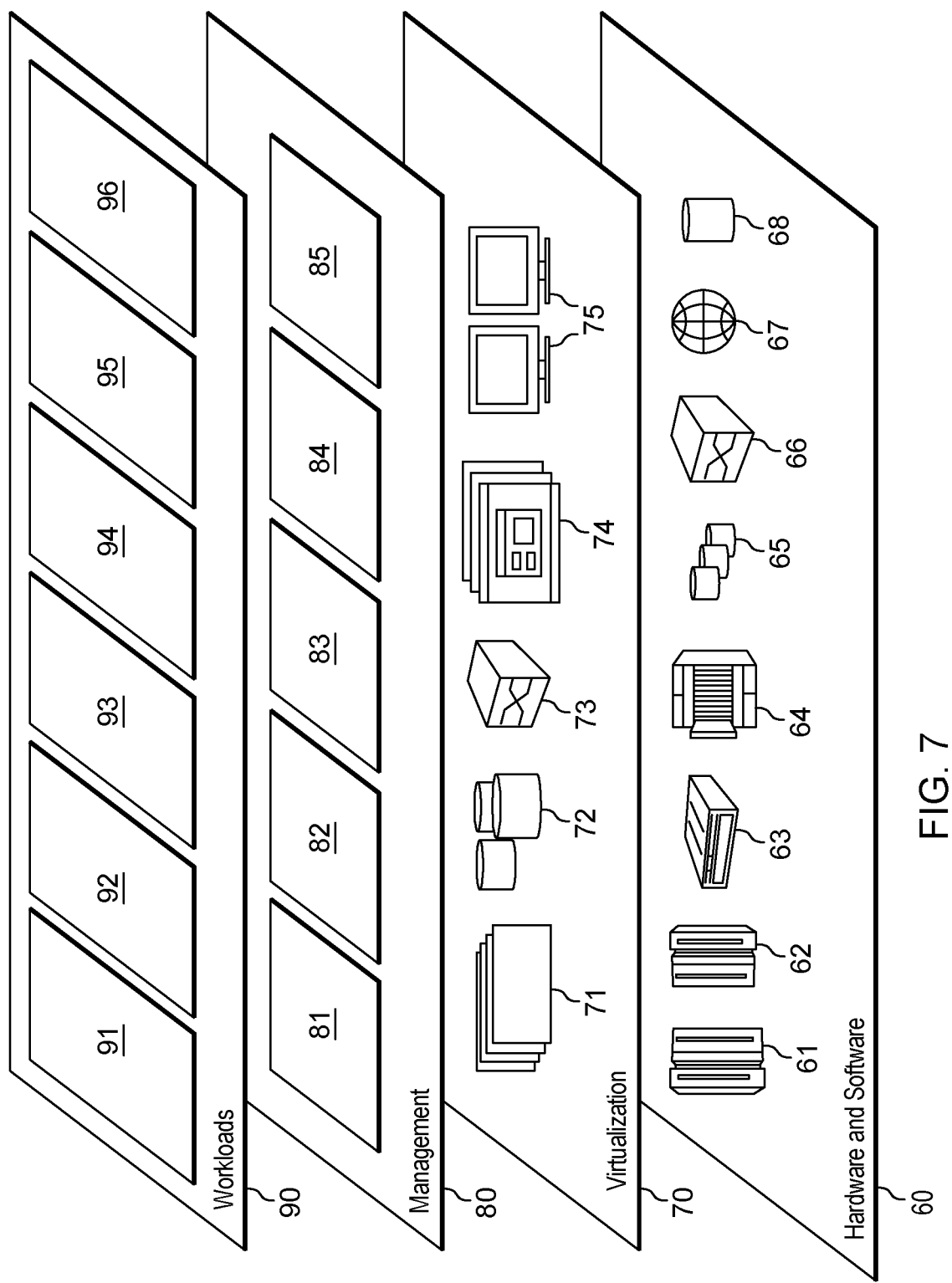
FIG. 7 depicts abstraction model layers according to an embodiment of the present invention.

Referring now to FIG. 7, a set of functional abstraction layers provided by cloud computing environment 50 (FIG. 6) is shown. It should be understood in advance that the components, layers, and functions shown in FIG. 7 are intended to be illustrative only and embodiments of the invention are not limited thereto. As depicted, the following layers and corresponding functions are provided:

Hardware and software layer 60 includes hardware and software components. Examples of hardware components include: mainframes 61; RISC (Reduced Instruction Set Computer) architecture based servers 62; servers 63; blade servers 64; storage devices 65; and networks and networking components 66. In some embodiments, software components include network application server software 67 and database software 68.

Virtualization layer 70 provides an abstraction layer from which the following examples of virtual entities may be provided: virtual servers 71; virtual storage 72; virtual networks 73, including virtual private networks; virtual applications and operating systems 74; and virtual clients 75.

In one example, management layer 80 may provide the functions described below. Resource provisioning 81 provides dynamic procurement of computing resources and other resources that are utilized to perform tasks within the cloud computing environment. Metering and Pricing 82 provide cost tracking as resources are utilized within the cloud computing environment, and billing or invoicing for consumption of these resources. In one example, these resources may include application software licenses. Security provides identity verification for cloud consumers and tasks, as well as protection for data and other resources. User portal 83 provides access to the cloud computing environment for consumers and system administrators. Service level management 84 provides cloud computing resource allocation and management such that required service levels are met. Service Level Agreement (SLA) planning and fulfillment 85 provide pre-arrangement for, and procurement of, cloud computing resources for which a future requirement is anticipated in accordance with an SLA.

Workloads layer 90 provides examples of functionality for which the cloud computing environment may be utilized. Examples of workloads and functions which may be provided from this layer include: mapping and navigation 91; software development and lifecycle management 92; virtual classroom education delivery 93; data analytics processing 94; transaction processing 95; and generation of a predictive model 96.

The present invention may be a system, a method, and/or a computer program product at any possible technical detail level of integration. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, configuration data for integrated circuitry, or either source code or object code written in any combination of one or more programming languages, including an object oriented programming language such as Smalltalk, C++, or the like, and procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the blocks may occur out of the order noted in the Figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

The terminology used herein is for the purpose of describing particular embodiments only and is not intended to be limiting. As used herein, the singular forms "a", "an" and "the" are intended to include the plural forms as well, unless the context clearly indicates otherwise. It will be further understood that the terms "comprises" and/or "comprising", when used in this specification, specify the presence of stated features, integers, steps, operations, elements, and/or components, but do not preclude the presence or addition of one or more other features, integers, steps, operations, elements, components and/or groups thereof.

The corresponding structures, materials, acts, and equivalents of all means or step plus function elements in the claims below, if any, are intended to include any structure, material, or act for performing the function in combination with other claimed elements as specifically claimed. The description of one or more embodiments has been presented for purposes of illustration and description, but is not intended to be exhaustive or limited to in the form disclosed. Many modifications and variations will be apparent to those of ordinary skill in the art. The embodiment was chosen and described in order to best explain various aspects and the practical application, and to enable others of ordinary skill in the art to understand various embodiments with various modifications as are suited to the particular use contemplated.

What is claimed is:

1. A computer-implemented method, comprising:
   continuously obtaining, by one or more processors, training data for a machine learning algorithm, wherein the training data comprises data related to physical activities performed by an individual from one or more sensors proximate to the individual, wherein a portion of the data related to the physical activities performed by the individual is selected from the group consisting of: physiological data, heart rate, blood pressure, blood oxygen saturation, respiration, movement data indicating a restful state, movement data indicating an active state, temperature, ambient light readings, eye focus, and noise readings, wherein the data related to the physical activities is collected by the one or more sensors contemporaneously with engagement of the individual in the physical activities;
   obtaining, by the one or more processors, data indicating consumption of a substance by the individual at a first time;
   generating, by the one or more processors, a predictive model utilizing baseline behavioral patterns of the individual when the individual is engaged in each of the physical activities and expected deviations from the baseline behavioral patterns of the individual when the individual has consumed the substance, wherein the predictive model is utilized to determine one or more probabilities that the individual will exhibit one or more behaviors comprising the expected deviations, and to determine an interval subsequent to consuming the substance in which the individual will exhibit the one or more behaviors, the generating comprising:
      training, by the one or more processors, the machine leaning algorithm, utilizing a first set of the training data and a second set of training data, wherein the first set of the training data was obtained prior to consumption of the substance by the individual, and wherein the second set of the training data was obtained subsequent to the first time, to identify impacts of the consumption of the substance at the first time on the identified baseline behavioral patterns of the individual, wherein the first set of training data trains the machine leaning algorithm to identify baseline behavioral patterns of the individual when the individual is engaged in each of the physical activities, and wherein the second set of training data trains the machine learning algorithm to identify of the consumption of the substance at the first time on the identified baseline behavioral patterns of the individual; and generating, by the one or more processors, based on the training of the machine leaning algorithm, the predictive model;

obtaining, by the one or more processors, data indicating consumption of the substance by the individual at a second time;

determining, by the one or more processors, based on applying the predictive model, a probability that the individual will exhibit one or more behaviors comprising the expected deviations, and an interval subsequent to the second time in which the individual will exhibit the one or more behaviors;

determining, by the one or more processors, that the individual is engaged in a physical activity of the physical activities, wherein the one or more behaviors comprising the expected deviations impact the physical activity;

based on applying the predictive model determining that probability will exceed a pre-defined threshold during the interval subsequent to the second time and impact the physical activity during the interval subsequent to the second time, and the determination that the individual is engaged in the physical activity, transmitting, by the one or more processors, the probability and the interval subsequent to the second time, to the individual, via a computing device comprising a portion of the one or more sensors;

obtaining, by the one or more processors, data indicating consumption of the substance by the individual at a third time;

obtaining, during the continuously obtaining, training data at a given time;

cognitively analyzing, by the one or more processors, the training data obtained at the given time, wherein the cognitively analyzing comprises determining that the training data obtained at the given time comprises values which are outliers to the baseline behavioral patterns of the individual when the individual is engaged in each of the physical activities and to the expected deviations from the baseline behavioral patterns of the individual when the individual has consumed a substance;

determining, by the one or more processors, a number of times values obtained during the continuously obtaining are consistent with the outlier values obtained at the given time;

based on determining that the number of times the values obtained during the continuously obtaining are consistent with the outlier values obtained at the given time exceeds a threshold number, determining, by the one or more processors, the probability that the individual will exhibit one or more behaviors comprising the expected deviations, the determining comprising:

updating, by the one or more processors, the predictive model, wherein the updating comprises re-training, by the one or more processors, the machine learning algorithm with the training data obtained at a given time; and applying, by the one or more processors, the predictive model, to determine the probability that the individual will exhibit one or more behaviors comprising the expected deviations, and an interval subsequent to a third time in which the individual will exhibit the one or more behaviors; and based on determining that the number of times the values obtained during the continuously obtaining are consistent with the outlier values obtained at the given time does not exceed a threshold number, determining, by the one or more processors, the probability based on the training data obtained at the given time.

2. The computer-implemented method of claim 1, wherein the one or more sensors monitor biometrics, behaviors, and motion of the individual when the individual is engaged in the physical activities.

3. The computer-implemented method of claim 1, wherein the computing device comprising the portion of the one or more sensors is an Internet of Things device.

4. The computer-implemented method of claim 1, wherein the data indicating consumption of the substance by the individual at the first time comprises contextual data describing the consumption.

5. The computer-implemented method of claim 4, wherein the contextual data comprises a quantity of the substance consumed by the individual at the first time.

6. The computer-implemented method of claim 1, wherein obtaining the data indicating consumption of the substance by the individual at the first time comprises obtaining, by the one or more processors, a schedule of planned consumption times for the substance, wherein the first time comprises a planned consumption time, wherein the schedule is accessible via a communication connection to at least one computing resource, and wherein the at least one computing resource is communicatively coupled to the one or more processors.

7. The computer-implemented method of claim 1, wherein obtaining the data indicating consumption of the substance by the individual at the first time comprises obtaining, by the one or more processors, the data from a device selected from the group consisting of: at least one sensor of the one or more sensors and an image capture device proximate to the individual.

8. The computer-implemented method of claim 1, wherein obtaining the data indicating consumption of the substance by the individual at the first time comprises capturing, by the one or more processors, the data from a personal computing device utilized by the individual, wherein the one or more processors are communicatively coupled to the personal computing device.

9. The computer-implemented method of claim 1, further comprising:

obtaining, by the one or more processors, data related to one or more additional behaviors experienced by other individuals after consuming the substance;

cognitively analyzing, by the one or more processors, the data related to the one or more additional behaviors experienced by the other individuals after consuming the substance to determine if the additional data is consistent with the baseline behavioral patterns or with the expected deviations from the baseline behavioral patterns; and based on determining that the additional data is inconsistent with the baseline behavioral patterns, updating, by the one or more processors, the predictive model to predict the one or more additional behaviors, wherein the updating comprises re-training, by the one or more processors, the machine learning algorithm based on utilizing the data related to the one or more additional behaviors experienced by the other individuals after consuming the substance as training data in the re-training.

10. A computer program product comprising:

a computer readable storage medium readable by one or more processors and storing instructions for execution by the one or more processors for performing a method comprising:

continuously obtaining, by the one or more processors, training data for a machine learning algorithm, wherein the training data comprises data related to physical activities performed by an individual from one or more sensors proximate to the individual, wherein a portion of the data related to the physical activities performed by the individual is selected from the group consisting of: physiological data, heart rate, blood pressure, blood oxygen saturation, respiration, movement data indicating a restful state, movement data indicating an active state, temperature, ambient light readings, eye focus, and noise readings, wherein the data related to the physical activities is collected by the one or more sensors contemporaneously with engagement of the individual in the physical activities;

obtaining, by the one or more processors, data indicating consumption of a substance by the individual at a first time;

generating, by the one or more processors, a predictive model utilizing baseline behavioral patterns of the individual when the individual is engaged in each of the physical activities and expected deviations from the baseline behavioral patterns of the individual when the individual has consumed the substance, wherein the predictive model is utilized to determine one or more probabilities that the individual will exhibit one or more behaviors comprising the expected deviations, and to determine an interval subsequent to consuming the substance in which the individual will exhibit the one or more behaviors, the generating comprising:

training, by the one or more processors, the machine leaning algorithm, utilizing a first set of the training data and a second set of training data, wherein the first set of the training data was obtained prior to consumption of the substance by the individual, and wherein the second set of the training data was obtained subsequent to the first time, to identify impacts of the consumption of the substance at the first time on the identified baseline behavioral patterns of the individual, wherein the first set of training data trains the machine leaning algorithm to identify baseline behavioral patterns of the individual when the individual is engaged in each of the physical activities, and wherein the second set of training data trains the machine learning algorithm to identify impacts of the consumption of the substance at the first time on the identified baseline behavioral patterns of the individual; and generating, by the one or more processors, based on the training of the machine leaning algorithm, the predictive model;

obtaining, by the one or more processors, data indicating consumption of the substance by the individual at a second time;

determining, by the one or more processors, based on applying the predictive model, a probability that the individual will exhibit one or more behaviors comprising the expected deviations, and an interval subsequent to the second time in which the individual will exhibit the one or more behaviors;

determining, by the one or more processors, that the individual is engaged in a physical activity of the physical activities, wherein the one or more behaviors comprising the expected deviations impact the physical activity;

based on applying the predictive model determining that the probability will exceed a pre-defined threshold during the interval subsequent to the second time and impact the physical activity during the interval subsequent to the second time, and the determination that the individual is engaged in the physical activity, transmitting, by the one or more processors, the probability and the interval subsequent to the second time, to the individual, via a computing device comprising a portion of the one or more sensors;

obtaining, by the one or more processors, data indicating consumption of the substance by the individual at a third time;

obtaining, during the continuously obtaining, training data at a given time;

cognitively analyzing, by the one or more processors, the training data obtained at the given time, wherein the cognitively analyzing comprises determining that the training data obtained at the given time comprises values which are outliers to the baseline behavioral patterns of the individual when the individual is engaged in each of the physical activities and to the expected deviations from the baseline behavioral patterns of the individual when the individual has consumed a substance;

determining, by the one or more processors, a number of times values obtained during the continuously obtaining are consistent with the outlier values obtained at the given time;

based on determining that the number of times the values obtained during the continuously obtaining are consistent with the outlier values obtained at the given time exceeds a threshold number, determining, by the one or more processors, the probability that the individual will exhibit one or more behaviors comprising the expected deviations, the determining comprising:

updating, by the one or more processors, the predictive model, wherein the updating comprises re-training, by the one or more processors, the machine learning algorithm with the training data obtained at a given time; and applying, by the one or more processors, the predictive model, to determine the probability that the individual will exhibit one or more behaviors comprising the expected deviations, and an interval subsequent to a third time in which the individual will exhibit the one or more behaviors; and based on determining that the number of times the values obtained during the continuously obtaining are consistent with the outlier values obtained at the given time does not exceed a threshold number, determining, by the one or more processors, the probability based on the training data obtained at the given time.

11. The computer program product of claim 10, wherein the one or more sensors monitor biometrics, behaviors, and motion of the individual when the individual is engaged in the physical activities.

12. A system comprising:
a memory;
one or more processors in communication with the memory;
program instructions executable by the one or more processors via the memory to perform a method, the method comprising:
continuously obtaining, by the one or more processors, training data for a machine learning algorithm, wherein the training data comprises data related to physical activities performed by an individual from one or more sensors proximate to the individual, wherein a portion of the data related to the physical activities performed by the individual is selected from the group consisting of: physiological data, heart rate, blood pressure, blood oxygen saturation, respiration, movement data indicating a restful state, movement data indicating an active state, temperature, ambient light readings, eye focus, and noise readings, wherein the data related to the physical activities is collected by the one or more sensors contemporaneously with engagement of the individual in the physical activities;
obtaining, by the one or more processors, data indicating consumption of a substance by the individual at a first time;
generating, by the one or more processors, a predictive model utilizing baseline behavioral patterns of the individual when the individual is engaged in each of the physical activities and expected deviations from the baseline behavioral patterns of the individual when the individual has consumed the substance, wherein the predictive model is utilized to determine one or more probabilities that the individual will exhibit one or more behaviors comprising the expected deviations, and to determine an interval subsequent to consuming the substance in which the individual will exhibit the one or more behaviors, the generating comprising:
training, by the one or more processors, the machine leaning algorithm, utilizing a first set of the training data and a second set of training data, wherein the first set of the training data was obtained prior to consumption of the substance by the individual, and wherein the second set of the training data was obtained subsequent to the first time, to identify impacts of the consumption of the substance at the first time on the identified baseline behavioral patterns of the individual, wherein the first set of training data trains the machine leaning algorithm to identify baseline behavioral patterns of the individual when the individual is engaged in each of the physical activities, and wherein the second set of training data trains the machine learning algorithm to identify impacts of the consumption of the substance at the first time on the identified baseline behavioral patterns of the individual; and
generating, by the one or more processors, based on the training of the machine leaning algorithm, the predictive model;
obtaining, by the one or more processors, data indicating consumption of the substance by the individual at a second time;
determining, by the one or more processors, based on applying the predictive model, a probability that the individual will exhibit one or more behaviors comprising the expected deviations, and an interval subsequent to the second time in which the individual will exhibit the one or more behaviors;
determining, by the one or more processors, that the individual is engaged in a physical activity of the physical activities, wherein the one or more behaviors comprising the expected deviations impact the physical activity;
based on applying the predictive model determining that the probability will exceed a pre-defined threshold during the interval subsequent to the second time and impact the physical activity during the interval subsequent to the second time, and the determination that the individual is engaged in the physical activity, transmitting, by the one or more processors, the probability and the interval subsequent to the second time, to the individual, via a computing device comprising a portion of the one or more sensors;
obtaining, by the one or more processors, data indicating consumption of the substance by the individual at a third time;
obtaining, during the continuously obtaining, training data at a given time;
cognitively analyzing, by the one or more processors, the training data obtained at the given time, wherein the cognitively analyzing comprises determining that the training data obtained at the given time comprises values which are outliers to the baseline behavioral patterns of the individual when the individual is engaged in each of the physical activities and to the expected deviations from the baseline behavioral patterns of the individual when the individual has consumed a substance;
determining, by the one or more processors, a number of times values obtained during the continuously obtaining are consistent with the outlier values obtained at the given time;
based on determining that the number of times the values obtained during the continuously obtaining are consistent with the outlier values obtained at the given time exceeds a threshold number, determining, by the one or more processors, the probability that the individual will exhibit one or more behaviors comprising the expected deviations, the determining comprising:
updating, by the one or more processors, the predictive model, wherein the updating comprises re-training, by the one or more processors, the machine learning algorithm with the training data obtained at a given time; and
applying, by the one or more processors, the predictive model, to determine the probability that the individual will exhibit one or more behaviors comprising the expected deviations, and an interval subsequent to a third time in which the individual will exhibit the one or more behaviors; and
based on determining that the number of times the values obtained during the continuously obtaining are consistent with the outlier values obtained at the given time does not exceed a threshold number, determining, by the one or more processors, the probability based on the training data obtained at the given time.

* * * * *